United States Patent [19]

Hamill

[11] 4,237,225

[45] Dec. 2, 1980

[54] PROCESS FOR PREPARING TUNICAMYCIN

[75] Inventor: Robert L. Hamill, Greenwood, Ind.

[73] Assignee: Eli Lilly and Company, Indianapolis, Ind.

[21] Appl. No.: 965,547

[22] Filed: Dec. 1, 1978

[51] Int. Cl.³ ............................................. C12P 19/60
[52] U.S. Cl. ...................................... 435/75; 435/893; 435/886
[58] Field of Search .......................................... 435/75

[56] References Cited

U.S. PATENT DOCUMENTS 3,923,823  12/1975  Gale et al. .............................. 260/299
3,960,667  1/1976  Gale et al. .............................. 435/118

OTHER PUBLICATIONS

J. Antibiotics, 24 215–238 (1971).
Derwent Abstracts Accession No. 36739V/20.
Derwent Abstracts Accession No. 58415Y/33.
J. Antibiotics, 28 274–279 (1975).
Agric. Biol. Chem. 41, 2307–2309 (1977).

*Primary Examiner*—Alvin E. Tanenholtz
*Attorney, Agent, or Firm*—Nancy J. Harrison; Arthur R. Whale

[57] ABSTRACT

Tunicamycin is co-produced with antibiotic A-23187 by the cultivation of *Streptomyces chartreusis* NRRL 3882. Methods of recovering tunicamycin and for separating and isolating individual factors A, B, C, and D from tunicamycin complex are described.

5 Claims, No Drawings

PROCESS FOR PREPARING TUNICAMYCIN

Tunicamycin is a known antibiotic being described by A. Takatsuki et al., *The Journal of Antibiotics*, Vol. 24, pages 215-238 (1971). The antibiotic is produced by a strain of *Streptomyces lysosuperificus* (see Takatsuki, supra) and by Streptomyces LA-507 (see Japanese Pat. No. 2079-086). Minor antibiotic factors isolated from the streptovirudin complex produced by Streptomyces JA 1024 are reported to be related to tunicamycin [See K. Ekhardt, et al., *The Journal of Antibiotics*, Vol. 28, pages 274-279 (1975) and *Zeitschrift fur Allg. Mikrobiologie*, Vol. 13, pages 625-627 (1973)].

Tunicamycin is a complex comprising a mixture of co-produced individual antibiotic factors. The four major factors of the tunicamycin complex have been shown by A. Takatsuki et al. *Agric. Biol. Chem.*, Vol. 41, pages 2307-2309 (1977) to be antibiotics having the structural formula (I) depicted below:

The present invention relates to novel methods of preparing tunicamycin and tunicamycin A, tunicamycin B, tunicamycin C, and tunicamycin D. In particular, the invention constitutes a method of preparing tunicamycin which comprises cultivating *Streptomyces chartreusis* NRRL 3882 in a culture medium containing assimilable sources of carbon, nitrogen, and inorganic salts under submerged aerobic conditions until a substantial amount of tunicamycin is produced; separating tunicamycin from co-produced antibiotic A-23187; and recovering tunicamycin. The invention also contemplates methods of preparing tunicamycin A, tunicamycin B, tunicamycin C, or tunicamycin D which comprises preparing tunicamycin by cultivating *Streptomyces chartreusis* NRRL 3882 according to the method described above; separating the desired factor (i.e. tunicamycin A, B, C, or D) from other co-produced factors; and recovering the desired factor (i.e. tunicamycin A, B, C, or D). For the purpose of this invention, it is understood that each of the above-named individual factors is isolated in a

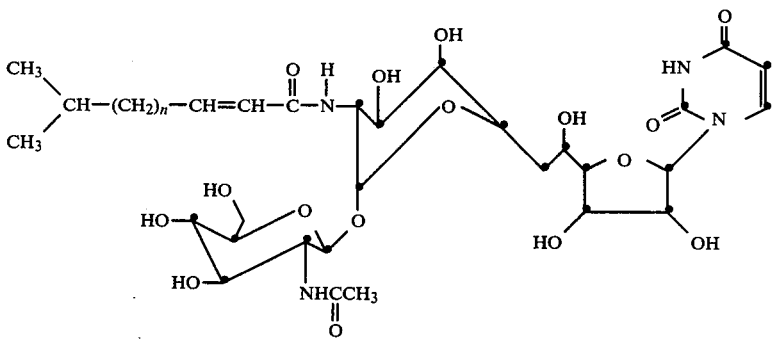

The individual factors are named according to Takatsuki et al. as follows:

(1) Tunicamycin A, when n=9
(2) Tunicamycin B, when n=10
(3) Tunicamycin C, when n=8
(4) Tunicamycin D, when n=11

It is seen that tunicamycin A, B, C, and D differ only with respect to the chain length of the fatty acid residue substituted on the amino group of the tunicamine moiety. The structures of the individual factors were determined by Takatsuki from analysis of the degradation products formed after acid hydrolysis of tunicamycin. The separation of tunicamycin into the individual factors and the isolation thereof has not been reported in the prior art.

As used herein and in the claims, "tunicamycin" means the complex comprising the co-produced major antibiotic factors known as "tunicamycin A", "tunicamycin B", "tunicamycin C", and "tunicamycin D". Additional minor factors are also present in the complex. It will be recognized by those skilled in the fermentation art that the number and ratio of individual factors produced in an antibiotic complex will vary depending on the fermentation conditions employed.

Tunicamycin has been reported to exhibit antibacterial and anti-viral activity in in vitro tests. [see Takatsuki, et al., supra]. Tunicamycin is a potent inhibitor of glycoprotein synthesis, preventing the incorporation of sugar into protein cell wall constituents. The use of tunicamycin to study the mechanism of cell wall synthesis has been widely reported in the biochemical literature.

form substantially free of other co-produced tunicamycin factors.

The cultivation of *Streptomyces chartreusis* NRRL 3882 coproduces, along with tunicamycin, antibiotic A-23187 which is described in U.S. Pat. No. 3,923,823. This antibiotic, however, has a chemical structure markedly different from the structures of tunicamycin A, B, C, or D. Tunicamycin can be separated from co-produced antibiotic A-23187 by selective solvent extraction, selective precipitation, or chromatography.

The *Streptomyces chartreusis* culture useful for the production of tunicamycin has been deposited and made a part of the stock culture collection of the Northern Regional Research Center, U.S. Department of Agriculture, Agriculture Reserve Service, Peoria, Ill. 61604, from which it is available to the public under the number NRRL 3882.

As is the case with other organisms, the characteristics of the tunicamycin producing culture *Streptomyces chartreusis* NRRL 3882, are subject to variation. For example, artificial variants and mutants of the NRRL 3882 strain may be obtained by treatment with various known mutagens, such as ultraviolet rays, X-rays, high frequency waves, radioactive rays, and chemicals. All natural and artificial variants and mutants of *Streptomyces chartreusis* NRRL 3882, which produce tunicamycin, may be used in this invention.

The full description of *Streptomyces chartreusis* NRRL 3882 and of the method for its cultivation in shake flasks and tanks is described in U.S. Pat. No. 3,923,823 (See also U.S. Pat. No. 3,960,667 which is a divisional thereof), the full disclosure of which is incorporated herein by reference.

After completion of the fermentation using *Streptomyces chartreusis* NRRL 3882, tunicamycin is present both in the mycelium and in the broth. Most of the tunicamycin is present, however, in the mycelium. The mycelium is collected by conventional means, such as by filtration (using a filter aid, if desired) or by centrifugation. Tunicamycin can be recovered from the mycelial filter cake and from the filtered broth by methods well known in fermentation technology, such as solvent extraction, precipitation, and chromatography.

Tunicamycin present in the mycelial filter cake can be removed therefrom by washing the cake with a water-miscible lower alkanol (e.g. methanol, ethanol, or propanol). Tunicamycin present in the aqueous mycelial alkanol extracts (obtained after evaporation of the alkanol) or in the filtration broth (obtained by removal of mycelium) can be recovered by extraction with a water-immiscible lower alkanol (e.g. n-butanol or n-amyl alcohol) or by chromatography using various adsorbents. Among suitable adsorbents are carbon, Diaion HP-20, Amberlite XAD-2, Amberlite XAD-4, or Amberlite X-384. Purification of crude tunicamycin (obtained after extraction into a water-immiscible alkanol or after chromatography) can be achieved by precipitation (e.g. from methanol to which is added acetone) or by re-chromatography. Suitable chromatographic adsorbents are those named above and, in addition, silica gel, alumina, Florisil, Sephadex G-15, Sephadex G-25, Sephadex LH-20, and reverse phase resins such as silica gel/$C_8$ or silica gel/$C_{18}$. Diaion is available from Mitsubishi Chemical Industries, Tokyo; the Amberlite resins are available from Rohm and Haas Co., Philadelphia, Pa.; the Sephadex resins are available from Pharmacia Fine Chemicals AB, Uppsala, Sweden, Florisil is available from Floridin Co. Tallahasse, Fla., and silica gel/$C_8$ and silica gel $C_{18}$ are available from E. Merck, Darmstadt, Germany. The preparation of a high loading capacity silica gel/$C_{18}$ from LP-1 Silica gel (Whatman) is described in Example 6.

Silica gel and Diaion HP-20 are preferred adsorbents for the initial purification of tunicamycin. With silica gel, the impure tunicamycin, dissolved in methanol-water (1:1), is mixed with sufficient silica gel to adsorb all the liquid. A slurry of the moist adsorbent is added to a silica gel column packed in acetonitrile-water (9:1). The collected fractions are monitored by bioassay using *Bacillus subtilis* as the detecting organism. With Diaion HP-20, the impure tunicamycin in water solutions (which can be the filtered broth after removal of mycelium or aqueous solutions obtained after the alcohol extraction of the mycelium) is placed on a column packed in water. After washing with water, the column is eluted with methanol-water (1:1), which removes impurities, and with methanol, which removes tunicamycin.

Reverse phase high pressure liquid chromatography using silica gel/$C_{18}$ adsorbent is a preferred method for the final purification of tunicamycin. In this method, tunicamycin (as obtained, for example, after chromatography using silica gel or Diaion HP-20), dissolved in water or methanol-water (2:1), is placed on a column equilibrated with methanol-water (2:1) at a pressure of 60–85 psi. The column is then eluted at the above pressure with methanol-water (2:1) to remove further impurities and with methanol water (4:1) to remove tunicamycin. The fractions as they are eluted are monitored with a ultraviolet spectrometer at 254 nm.

When a water-immiscible lower alkanol is used to extract tunicamycin from the filtered broth after removal of the mycelium or from aqueous solutions obtained after extraction of the mycelium with a water-miscible lower alkanol, both tunicamycin and antibiotic A-23187 are present in the extracts. Antibiotic A-23187 can be separated from tunicamycin by the following procedure: The alkanol extracts are concentrated and the residue is dissolved in methanol to which is added excess acetone. Tunicamycin precipitates from the solution, while most of the antibiotic A-23187 remains in the methanol-acetone supernatant. The precipitate is collected and is dissolved in water at pH 8. The solution is then adjusted to pH 3 and extracted with ethyl acetate which removes any remaining antibiotic A-23187. Tunicamycin is then recovered from the water phase by extraction with a water-immiscible lower alkanol (e.g. n-butanol or amyl alcohol).

When chromatography, such as with Diaion HP-20 adsorbent, is used to remove tunicamycin from the broth filtrate or from aqueous solution obtained after extraction of the mycelium, tunicamycin is separated from antibiotic A-23187 by virtue of the difference in polarity between the two materials. With Diaion HP-20, for example, antibiotic A-23187 (being more polar) is separated during the initial elutions using water and methanol-water (1:1). Separation of antibiotic A-23187 will also occur during reverse phase high pressure liquid chromatography using silica gel/$C_{18}$.

When it is desired to obtain the individual factors (tunicamycin A, B, C, or D), tunicamycin can be separated by chromatographic techniques. One procedure is to employ a modification of the reverse-phase high pressure liquid chromatography method, using silica gel/$C_{18}$ as herein-before described. Tunicamycin is applied to the column either in water solution or in methanol-water (2:1). Elution with 3:1 methanol-water (rather than with 4:1 methanol-water) will effect the separation of the individual factors. The fractions are monitored by bioassay using *Bacillus subtilis* as the detecting organism or by a ultraviolet detector by measuring absorption at 254 nm. Another procedure for separating the factors, is by chromatography using Sephadex LH-20 as the absorbent and methanol-water (15:85) as the eluent. Fractions are monitored by bioassay using *Bacillus subtilis* as the detecting organism or by reverse-phase high pressure liquid chromatography on silica-gel/$C_{18}$ with 3:1 methanol-water as eluent.

Reverse-phase high pressure liquid chromatography [silica gel/$C_{18}$, developed with methanol-water (3:1)] and thin-layer chromatography, [cellulose/aluminum, using water-ethanol-acetic acid (70:24:6) for development] reveals the presence of four additional minor fractions, tunicamycin $A_1$, tunicamycin $B_1$, tunicamycin $C_1$, and tunicamycin $D_1$. These factors are isomeric with the major factors ($A,A_1$; $B,B_1$; $C,C_1$; $D,D_1$) as indicated by field desorption mass spectrometry. The isomerization is likely associated with the configuration of the double bond in the fatty acid moiety. According to Takatsuki et al. [*Agri. Biol. Chem.*, Vol. 41, pages 2307–2309 (1977)] the fatty acid double bond of the major factors [tunicamycin A, B, C, and D] has the trans configuration. The fatty acid double bond of the minor factors may be in the cis configuration.

Tunicamycin and tunicamycin A, B, C, and D inhibit the growth of certain pathogenic organisms, particularly gram positive bacteria, fungi, and yeasts, as demonstrated in vitro by standard paper-disc inhibition tests. The zones of inhibition, as determined in these tests, are shown below:

| Organism | Zone Diameter (mm) | | | | | | | | |
|---|---|---|---|---|---|---|---|---|---|
| | C | $C_1$ | A | $A_1$ | B | $B_1$ | D | $D_1$ | Complex |
| *Staphylococcus aureus* | | | tr | tr | tr | tr | tr | tr | tr |
| *Bacillus subtilis* | 28 | 28 | 25 | 22 | 19 | 18 | 19 | 15 | 28 |
| *Micrococcus luteus* | tr | | | | 10 | | tr | tr | tr |
| *Saccharomyces pastorianus* | 16 | 18 | 18 | 15 | 23 | 16 | 13 | 13 | 20 |
| *Neurospora crassa* | 10 | 10 | 10 | 10 | 10 | tr | tr | tr | 11 |
| *Candida albicans* | 14 | 15 | 15 | 12 | 12 | tr | 11 | tr | 14 |
| *Bacillus subtilis* in minimal medium | 36 | 37 | 35 | 34 | 29 | 26 | 27 | 21 | 33 | tr = trace (6.5–9 mm)

The estimated $LD_{50}$ after single-dose administration of tunicamycin is 6.25 mg/kg (PO), 1.8 mg/kg (IV), 1.8 mg/kg (IP) in mice.

The following examples will illustrate the processes of the invention:

EXAMPLE 1

Fermentation of tunicamycin

The *Streptomyces chartreusis* (NRRL 3882) culture is prepared and maintained on an agar slant having the following composition:

| Tomato paste | 20.0 g. |
|---|---|
| Oatmeal | 20.0 g. |
| Agar | 20.0 g. |
| Deionized water | 1 liter |

The pH of the medium is adjusted to 6.7 with sodium hydroxide solution; after sterilization, the pH of the medium is 6.9.

The slant is inoculated with the A-23187-producing culture and incubated at 34° C. for 7 days. The sporulated slant is covered with a small amount of calf serum and gently scraped to provide an aqueous spore suspension. The suspension is transferred to small tubes and is lyophilized for preservation. One lyophilized pellet is used to inoculate each of four 250 ml. flasks each containing 50 ml. of sterile vegetative culture medium having the following composition:

| Glucose | 15.0 g |
|---|---|
| Starch, Soluble | 30.0 g |
| Soybean grits | 15.0 g |
| Corn steep liquor | 20.0 g |
| NaCl | 5.0 g |
| $CaCO_3$ | 2.0 g |
| Tap water | 1.1 liters |

The pH of the medium is adjusted to 6.5 with sodium hydroxide solution; after sterilization, the pH of the medium is 6.9.

The inoculated vegetative medium is incubated for 48 hours at 30° C. on a rotary shaker operating at 250 r.p.m. A ten ml portion of the resulting culture is then employed to inoculate each of three 2 l. flasks containing 400 ml of sterilized second-stage growth medium having the same composition as that described above.

The inoculated medium is allowed to ferment for 48 hours at 30° C. on a rotary shaker operating at 250 r.p.m. An 800 ml portion of the culture is used to inoculate 100 liters of the following medium in a 165 liter fermentor:

| | Percent |
|---|---|
| Glucose | 1.25 |
| Soybean grits | 1.5 |
| Acid-hydrolyzed casein | 0.1 |
| Blackstrap molasses | 0.3 |
| $CaCO_3$ | 0.25 |
| $MgSO_4 \cdot 7H_2O$ | 0.25 |
| Tap water | 100 liters |

The pH of the medium is 7.0 after sterilization.

The inoculated medium is aerated at a rate of ½ volume of air per volume of culture per minute and is stirred with conventional agitators at 300 r.p.m.

The fermentation is carried out at 30° C. for 2 days.

EXAMPLE 2

Recovery and purification of tunicamycin (Procedure A)

(a) Isolation from fermentation broth

Two hundred liters of fermentation broth are filtered with 3% Hyflo Supercel filter aid, and the filtrate (150 l.) is adjusted to pH 3 with HCl and extracted twice with 75 l. of n-butanol. The extracts are combined and concentrated in vacuo to a low volume. Five volumes of acetone are added to the concentrate and the mixture is held at 5° C. for 16 hours to precipitate the tunicamycin. The precipitate is collected and combined with the precipitate from the mycelial extract obtained thusly. The mycelial filter cake is extracted twice with 40 l. volumes of methanol, and the extracts are concentrated in vacuo to remove the methanol. The concentrate is adjusted to pH 3 with HCl and extracted twice with n-butanol. The combined extracts are concentrated in vacuo to a syrup. The syrup is dissolved in a small volume (1 l.) of methanol, 5 volumes of acetone are added, and the mixture is held at 5° C. to complete the precipitation of tunicamycin. The precipitate is collected and combined with the precipitate obtained from the original filtrate. The mixture of precipitates is dissolved in 5 l. of water adjusted to pH 8 with dilute NaOH. The pH of the resulting solution is adjusted to pH 3 with HCl, and the mixture is extracted twice with ethyl acetate to remove any residual antibiotic A-23187 and other impurities. The aqueous phase is then extracted three times with n-butanol. The butanol extracts are combined and concentrated to a residue in vacuo. The residue is dissolved in 1 l. of methanol, and 10 l. of acetone is added to precipitate the tunicamycin. After standing at 5° C. for 16 hours, the precipitate is collected and dried in vacuo to yield 10.45 g. of crude tunicamycin.

(b) Purification of crude tunicamycin

Fifteen grams of crude tunicamycin dissolved in 100 ml of methanol, is added to 100 ml of water. The solution (pH 3.1) is adjusted to pH 9 with 5 N NaOH. The solution is mixed with sufficient silica gel (Grace Grade 62) to adsorb all the liquid. The moist silica gel is slurried in acetonitrile and added to the top of a 6.7×90 cm column of silica gel (Grace Grade 62) packed in acetonitrile. (The column had originally been loaded in water, then washed thoroughly with acetonitrile.) The column is washed with 4 l. of acetonitrile and developed with acetonitrile:water (9:1) collecting 1 l. fractions. The elution is monitored by bioassay using *Bacillus*

*subtilis.* Fractions 17–32 containing most of the tunicamycin activity are combined and concentrated to a residue in vacuo. The residue is dissolved in a mixture of water and dioxane and freeze-dried to yield 4.139 g. of tunicamycin complex (tan powder). An additional 1.2 g. of complex are obtained from fractions 33–62.

Impure preparations from the silica gel column are purified by chromatography over a column of Diaion HP-20 resin (Mitsubishi Chemical Industries, Tokyo). A 200 mg sample of complex (light tan) is dissolved in water and applied to a column containing 5 ml of HP-20 resin. The column is washed with 50 ml of water, 50 ml of methanol:water (1:1), and 50 ml methanol, collecting ca. 8 ml fractions. Impurities are removed with the first two washes. Methanol removes the tunicamycin complex. The fractions 12–17 containing the complex are combined and freeze-dried to yield 70 mg of tunicamycin complex (white powder).

(c) Final Purification of Tunicamycin

Tunicamycin complex (5.34 g) from the silica gel column step is dissolved in 100 ml water by adjusting to pH 9 with dilute NaOH. The solution is applied to a 4.1×60 cm glass column of reverse-phase resin (silica gel/C18*) equilibrated in methanol:water (2:1). The column is washed with 50 ml of water before loading the sample and with 100 ml water after loading. The column is developed at 60–65 lb/sq. in. with methanol:water (2:1) and then with methanol:water (4:1), as indicated by monitoring the elution with a UV detector at 254 nm. Fractions of 25 ml were collected. A yellow to brown material (inactive) is eluted with the methanol:water (2:1) system (fractions 16–51), and the tunicamycin complex is eluted with the methanol:water (4:1) system. Fractions 74–165 containing the complex are combined, concentrated, and freeze-dried to yield 2.13 g. of tunicamycin complex (white powder). The complex is crystallized from hot methanol (decomposed at about 200° C.).

*Prepared as described in Example 6

ANALYSIS OF TUNICAMYCIN

A. Elemental: Found: C, 53.31%; H, 6.86;
   analysis       N, 6.61; O, 29.51.
B. Ultraviolet absorption: Am = 9,400 (258 nm)
C. Optical Rotation: $[\alpha]_D^{25} = +62.4°$ (C = 0.37, methanol)
D. Infrared Absorption Frequencies (in wavenumbers, cm$^{-1}$)
   KBr Pellet
   3450-3240, 3080, 2954, 2926, 2854, 1708, 1667, 1653,
   1552, 1468, 1380, 1315, 1263, 1118, 1092, 1022, 956,
   910, 844, 812, 770, 720, 714, 555
E. Thin Layer Chromatography
   (1)  TLC plate: cellulose on aluminum sheet
        System: n-Butanol saturated with water
        Organism: *Bacillus subtilis*
        $R_f = 0.32$
   (2)  TLC plate silica gel 60, F-254 (EM Laboratories)
        System. CHCl$_3$: methanol (1:2)
        Organism: *B. subtilis*
        $R_f = 0.55$
   (3)  TLC plate: cellulose on aluminum sheet
        (EM Laboratories)
        System: water;ethanol;acetic acid (70:24:6)
        Organism: *B. subtilis*

| Factor | $R_f$ |
|---|---|
| C | 0.78 |
| C$_1$ | 0.77 |
| A | 0.68 |
| A$_1$ | 0.62 |
| B | 0.5 |
| B$_1$ | 0.45 |
| D | 0.35 |
| D$_1$ | 0.32 |

(4) TLC plate: revere-phase silica-gel/C$_{18}$
    with fluorescent indicator (Whatman)
    System: methanol:water (3:1)
    Detector: 254 nm

| Factor | $R_f$ |
|---|---|
| C | 0.27 |
| A | 0.21 |
| B | 0.15 |
| D | 0.12 |

(5) TLC plate: reverse-phase silica-gel/C$_{18}$
    with fluorescent indicator (Whatman)
    System: water:methanol:acetonitrile (45:15:40)
    with 0.2% pyridine and 0.2% acetic acid

| Factor | $R_f$ |
|---|---|
| C | 0.41 |
| A | 0.32 |
| B | 0.22 |
| D | 0.16 |

F. Tunicamycin Separation by Reverse-Phase Resin (silica gel/C$_{18}$) Chromatography.
   Adsorbent: silica gel/C$_{18}$
   Detection: 254 nm
   Pressure: 100 psi
   Solvent system: methanol:water (3:1)

| Factor | Relative Movement |
|---|---|
| C | 1.00 |
| C$_1$ | 1.07 |
| A | 1.37 |
| A$_1$ | 1.47 |
| B | 2.00 |
| B$_1$ | 2.16 |
| D | 2.70 |
| D$_1$ | 2.77 |

G. Tunicamycin Separation by Paper Chromatography-Bioautogram
   Paper: Whatman #4
   System: water:ethanol:acetic acid (70:24:6)
   Organism: *B. subtilis*
   Run (1): Complex

| Factor | $R_f$ | Comments |
|---|---|---|
| C | 0.61 | C and C$_1$ run close together - some separation |
| A | 0.43 | A and A$_1$ run close together - some separation |
| B | 0.25 | B and B$_1$ run close together - some separation |
| D | 0.14 | D$_1$ and D$_2$ run close together - some separation |

Run (2): Individual Factors

| Factor | $R_f$ |
|---|---|
| C | 0.76 |
| C$_1$ | 0.71 |
| A | 0.64 |
| A$_1$ | 0.61 |
| B | 0.49 |
| B$_1$ | 0.42 |
| D$_1$ | 0.36 |
| D$_2$ | 0.35 |

EXAMPLE 3

Recovery and Purification of tunicamycin (Procedure B)

Whole broth (2 l.) is filtered with 3% Hyflo Super-cel filter aid. The small amount of tunicamycin present in the filtrate (1.7 l.) is adsorbed on a Diaion HP-20 column (2.5×39 cm). The column is washed with 1 l. of water then with 1 l. of methanol:water (1:1) to remove impurities, and finally 1 l. of methanol to elute the tunicamycin. The methanol eluate is freeze-dried to yield impure tunicamycin.

The mycelial filter cake containing most of the tunicamycin is extracted three times with 600 ml methanol by stirring for 30 minutes and filtering. The methanol extracts are combined and concentrated in vacuo to a residue which is dissolved in 100 ml water adjusted to pH 7.5 with NaOH. The solution is centrifuged to remove the undissolved material. The insoluble residue is extracted 3 times with 30 ml of water adjusted to pH 8.3 with 0.1 N NaOH. Each extract is centrifuged. The four supernatants are combined (185 ml) and passed over a Diaion HP-20 column (1.2×22 cm) packed in water. The column is washed successively with 200 ml each of water, 50% aqueous methanol, and methanol. The tunicamycin complex is eluted with methanol. The fractions are concentrated in vacuo to a residue. The residue is dissolved in 10 ml of water adjusted to pH 9 with NH₄OH. The solution is chromatographed on a column (2.2×30 cm OD) of silica gel/$C_{18}$ equilibrated in methanol:water (2:1) at 80 psi, monitoring with a UV detector at 254 nm. Fractions of 10 ml are collected. Methanol:water (2:1) is used for 32 fractions, and thereafter methanol:water (4:1) is used. Fractions 43-76 are combined, concentrated in vacuo to a low volume, and freeze-dried to yield 63 mg of pure tunicamycin.

EXAMPLE 4

Separation of tunicamycin factors: Recovery of Tunicamycin A, Tunicamycin B, Tunicamycin C, and Tunicamycin D (Procedure A)

Preparations of tunicamycin from the silica gel column step or the reverse-phase resin step are used for fractionation of factors. A sample (3.2 g) of purified complex is dissolved in 150 ml of methanol and 75 ml of water. The solution is pumped at 60–65 psi onto a 4.1×60 cm (O.D.) column of reverse-phase resin (silica gel/$C_{18}$) equilibrated in methanol:water (2:1). The column is developed with methanol:water (2:1) to remove impurities and then with methanol:water (3:1) to elute the individual factors. Fractions of 25 ml are collected and the elution is monitored by bioassay using *Bacillus subtilis* and with a UV detector at 254 nm. The fractions containing the individual factors are combined, concentrated, and lyophilized to yield pure individual factors as follows:

| Factor | Fractions | Yield (mg) |
|---|---|---|
| C | 103–116 | 175 |
| A | 139–164 | 495 |
| B | 196–223 | 317 |
| D | 273–307 | 140 |

Analysis of tunicamycin A, B, C, and D:

A. Formula and molecular weight (by field desorption mass spectrometry):

| | | | |
|---|---|---|---|
| Tunicamycin | C | $C_{37}H_{60}N_4O_{16}$ | 816 |
| | A | $C_{38}H_{62}N_4O_{16}$ | 830 |
| | B | $C_{39}H_{64}N_4O_{16}$ | 844 |
| | D | $C_{40}H_{66}N_4O_{16}$ | 858 |

B. Elemental Analysis:

| | Calculated | Found |
|---|---|---|
| Tunicamycin C | C 54.44% | 53.98% |
| | H 7.35 | 7.24 |
| | N 6.86 | 6.80 |
| | O 31.37 | 31.53 |
| Tunicamycin A | C 54.94 | 54.70 |
| | H 7.47 | 7.15 |
| | N 6.75 | 6.70 |
| | O 30.84 | 30.70 |
| Tunicamycin B | C 55.45 | 53.11* |
| | H 7.58 | 7.28 |
| | N 6.64 | 6.28* |
| | O 30.33 | 33.10* |
| Tunicamycin D | C 55.94 | 53.30* |
| | H 7.69 | 7.19 |
| | N 6.52 | 6.11 |
| | O 29.84 | 29.44 |

*Apparently not dried properly. Peak matching of mass ion gave correct empirical formula.

C. Ultraviolet Absorption in Ethanol

| Factor | Am (258 nm) |
|---|---|
| C | 6780 |
| A | 8620 |
| B | 8625 |
| D | 7595 |

D. Optical Rotation

| Factor | $[\alpha]_D^{25}$ |
|---|---|
| C | 65.1° (C = 0.26, methanol) |
| A | 61.1° (C = 0.21, methanol) |
| B | 55.1° (C = 0.36, methanol) |
| D | 53.6° (C = 0.25, methanol) |

E. Infrared Absorption Frequencies for Tunicamycins A, B, C, and D (Run in KBr pellet)
3450-3280, 2954, 2926, 2854, 1708, 1667, 1653, 1623, 1549, 1468, 1380, 1315, 1263, 1232, 1128, 1092, 1024, 980, 956, 910, 890, 878, 770, 550 (in wavenumbers, $cm^{-1}$)

EXAMPLE 5

Separation of tunicamycin factors: Recovery of Tunicamycin A, Tunicamycin B, Tunicamycin C, and Tunicamycin D (Method B)

Tunicamycin complex (50 mg) is dissolved in 5 ml of methanol to which is added 30 ml. of water. The solution is applied to a column (1.7×88 cm.) of Sephadex LH-20 (Pharmacia) packed in methanol:water (15:85). The column is developed by eluting with the aforesaid solvent system. The elution of factors is monitored by bioassay using *B. subtilis* as the detecting organism and reverse-phase HPLC on silica gel/$C_{18}$ with methanol:water (3:1). Tunicamycin C is eluted first, followed by Tunicamycin A, Tunicamycin B, and finally Tunicamycin D. Fractions containing individual factors are combined and lyophilized to yield white powders. Other solvent systems, with varying amounts of methanol:water ratios (e.g. 80:20 or 90:10) can also be employed.

EXAMPLE 6

Preparation of Silica Gel/$C_{18}$ Reverse Phase Resin for HPLC

Step 1: Hydrolysis

LP-1 silica gel (1000 g. from Quantum Corp., now Whatman) is added to a mixture of 1650 ml. of concentrated sulfuric acid and 1650 ml. of concentrated nitric acid in a 5 l. round bottom flask and shaken for proper suspension. The mixture is heated on a steam bath overnight (16 hours) with a water-jacketed condenser attached to the flask.

The mixture is cooled in an ice bath and carefully filtered using a sintered glass funnel. The silica gel is washed with deionized water until the pH is neutral. The silica gel is then washed with acetone (4 l.) and dried under vacuum at 100° C. for 2 days.

Step 2: First Silylation

The dry silica gel from Step 1 is transferred to a round bottom flask and suspended in toluene (3.5 l.). The flask is heated on a steam bath for 2 hours to azetrope off some residual water. Octadecyl trichloro silane (321 ml, Aldrich Chemical Company) is added and the reaction mixture refluxed overnight (16 hours) with slow mechanical stirring at about 60° C. Care is taken so that the stirrer does not reach near the bottom of the flask. This is to prevent grinding the silica gel particles.

The mixture is allowed to cool. The silanized silica gel is collected, washed with toluene (3 l.) and acetone (3 l.), and then air-dried overnight (16–20 hours). The dried silica gel is suspended in 3.5 l. of acetonitrile:water (1:1) in a 5 l. flask, stirred carefully at room temperature for 2 hours, filtered, washed with acetone (3 l.) and air-dried overnight.

Step 3: Second Silylation

The procedure from the first silylation is repeated using 200 ml. of octadecyl trichloro silane. The suspension is refluxed at 60° C. for 2 hours while stirring carefully. The final product is recovered by filtration, washed with toluene (3 l.), methanol (6 l.), and then dried under vacuum at 50° C. overnight (16–20 hours).

What is claimed is:

1. A method for preparing tunicamycin which comprises cultivating *Streptomyces chartreusis* NRRL 3882 in a culture medium containing assimilable sources of carbon, nitrogen, and inorganic salts under submerged aerobic conditions until a substantial amount of tunicamycin is produced; separating tunicamycin from co-produced antibiotic A-23187; and isolating tunicamycin.

2. A method for preparing tunicamycin A which comprises preparing tunicamycin according to the method defined in claim 1; separating tunicamycin A from other co-produced tunicamycin factors; and isolating tunicamycin A.

3. A method for preparing tunicamycin B which comprises preparing tunicamycin according to the method defined in claim 1; separating tunicamycin B from other co-produced tunicamycin factors; and isolating tunicamycin B.

4. A method for preparing tunicamycin C which comprises preparing tunicamycin according to the method defined in claim 1; separating tunicamycin C from other co-produced tunicamycin factors; and isolating tunicamycin C.

5. A method for preparing tunicamycin D which comprises preparing tunicamycin according to the method defined in claim 1; separating tunicamycin D from other co-produced tunicamycin factors; and isolating tunicamycin D.

* * * * *